(12) United States Patent
Tong et al.

(10) Patent No.: US 10,433,769 B2
(45) Date of Patent: Oct. 8, 2019

(54) INTELLIGENT FITNESS SET AND ANTI-CHEATING METHOD THEREOF

(71) Applicant: EGGPLANT TECHNOLOGIES, Guangzhou, Guangdong (CN)

(72) Inventors: Dangdang Tong, Guangdong (CN); Feng Liu, Guangdong (CN); Ivan Ho, Guangdong (CN); Oscar Wong, Guangdong (CN)

(73) Assignee: EGGPLANT TECHNOLOGIES, Guangzhou (CN)

( * ) Notice: Subject to any disclaimer, the term of this patent is extended or adjusted under 35 U.S.C. 154(b) by 0 days.

(21) Appl. No.: 16/104,312

(22) Filed: Aug. 17, 2018

(65) Prior Publication Data
US 2018/0368738 A1 Dec. 27, 2018

Related U.S. Application Data

(63) Continuation of application No. PCT/CN2016/078633, filed on Apr. 7, 2016.

(30) Foreign Application Priority Data

Feb. 19, 2016 (CN) .......................... 2016 1 0094929

(51) Int. Cl.
*A61B 5/11* (2006.01)
*A63B 21/04* (2006.01)
(Continued)

(52) U.S. Cl.
CPC ........... *A61B 5/1118* (2013.01); *A61B 5/1116* (2013.01); *A61B 5/1126* (2013.01);
(Continued)

(58) Field of Classification Search
CPC ... A63B 22/20; A63B 22/203; A63B 23/1227; A63B 23/1236; A63B 2060/464;
(Continued)

(56) References Cited

U.S. PATENT DOCUMENTS

| 5,620,397 A | 4/1997 | Chieh |
| 2011/0070569 A1 | 3/2011 | Martens |
| 2014/0018210 A1 | 1/2014 | Lin |

FOREIGN PATENT DOCUMENTS

| CN | 1774206 A | 5/2006 |
| CN | 2860545 Y | 1/2007 |

(Continued)

*Primary Examiner* — Sundhara M Ganesan
*Assistant Examiner* — Shila Jalalzadeh Abyaneh
(74) *Attorney, Agent, or Firm* — Wayne & Ken, LLC; Tony Hom

(57) ABSTRACT

An intelligent fitness set and anti-cheating method thereof is disclosed. The intelligent fitness set includes a support, a base, a plurality of handheld fitness equipments and two handles, wherein a processor, a movement posture sensor and a touch sensor are provided in each handle, and the movement posture sensor and the touch sensor are connected respectively with the processor. One end of each handle is closed, while a bayonet is provided in the other end of the handle and the switchable hot-pluggable bayonet is configured to connect respectively to the plurality of handheld fitness equipments. In the present disclosure, one set of action training of a plurality of handheld fitness equipments is performed through the same set of handles, so that a user can complete movement of one time only by strictly complying with active standards during movement.

8 Claims, 16 Drawing Sheets

(51) Int. Cl.

| | |
|---|---|
| *A63B 21/055* | (2006.01) |
| *A63B 21/068* | (2006.01) |
| *A63B 23/02* | (2006.01) |
| *A63B 23/12* | (2006.01) |
| *A63B 21/00* | (2006.01) |
| *A63B 24/00* | (2006.01) |
| *A61B 5/00* | (2006.01) |
| *A63B 5/20* | (2006.01) |
| *A63B 22/20* | (2006.01) |
| *A61B 5/024* | (2006.01) |
| *A61B 5/22* | (2006.01) |
| *A63B 71/06* | (2006.01) |

(52) U.S. Cl.
CPC ............. *A61B 5/6895* (2013.01); *A63B 5/20* (2013.01); *A63B 21/0414* (2013.01); *A63B 21/0552* (2013.01); *A63B 21/0557* (2013.01); *A63B 21/068* (2013.01); *A63B 21/4035* (2015.10); *A63B 22/20* (2013.01); *A63B 23/0211* (2013.01); *A63B 23/1236* (2013.01); *A61B 5/02438* (2013.01); *A61B 5/225* (2013.01); *A61B 2560/0214* (2013.01); *A61B 2562/0219* (2013.01); *A63B 2024/0068* (2013.01); *A63B 2071/0627* (2013.01); *A63B 2208/0219* (2013.01); *A63B 2220/17* (2013.01); *A63B 2220/20* (2013.01); *A63B 2220/24* (2013.01); *A63B 2220/51* (2013.01); *A63B 2220/801* (2013.01); *A63B 2220/803* (2013.01); *A63B 2220/805* (2013.01); *A63B 2225/20* (2013.01); *A63B 2225/50* (2013.01); *A63B 2230/06* (2013.01)

(58) Field of Classification Search
CPC .......... A63B 2220/56; A63B 2220/801; A63B 2220/89; A63B 2220/80; A63B 2220/805; A63B 53/14; A63B 23/0211; A63B 21/068; A63B 21/0557; A63B 21/0552; A63B 21/0414; A63B 21/4035; A63B 5/20; A63B 2230/06; A63B 2225/50; A63B 2225/20; A63B 2220/803; A63B 2220/51; A63B 2220/24; A63B 2220/20; A63B 2220/17; A63B 2208/0219; A63B 2071/0627; A63B 2024/0068; A63B 21/01; A63B 21/00043; A63B 21/02; A61B 5/1118; A61B 5/1116; A61B 5/6895; A61B 5/1126; A61B 2560/0214; A61B 5/225; A61B 5/02438; A61B 2562/0219

See application file for complete search history.

(56) References Cited

FOREIGN PATENT DOCUMENTS

| | | |
|---|---|---|
| CN | 101342411 A | 1/2009 |
| CN | 101816831 A | 9/2010 |
| CN | 202637907 U | 1/2013 |
| CN | 103520876 A | 1/2014 |
| CN | 203915932 U | 11/2014 |
| CN | 204159006 U | 2/2015 |
| CN | 105194838 A | 12/2015 |
| CN | 205379610 U | 7/2016 |

INTELLIGENT FITNESS SET AND ANTI-CHEATING METHOD THEREOF

TECHNICAL FIELD

The present disclosure relates to an intelligent fitness set, and more particularly, to an intelligent fitness set and anti-cheating method thereof.

BACKGROUND

At present, in some common fitness equipment, mechanical devices are utilized to achieve simple counting functions, which, however, can't collect other movement information, and it is difficult for them to prevent people from cheating. Although some simple electronic devices are applied in some intelligent fitness equipment, most of them are merely utilized to collect counting information, which can't combine together other movement-related parameter requirements or collect movement information from various aspects, thus failing to reach the purpose of anti-cheating in a real sense.

At present, when using the popular intelligent fitness equipment, users often forward such information as times of movement to the web to compete with their friends on Moments or group together to compete with other users online. This requires that the intelligent fitness equipment has various anti-cheating techniques so as to improve the authenticity and validity of movement information.

SUMMARY

One objective of the present disclosure is to solve the above drawbacks existing in the prior art by providing an intelligent fitness set. The intelligent fitness set has a simple structure and low costs, and is able to an entire set of training exercises with a plurality of handheld fitness equipments by the same set of handles.

Another objective of the present disclosure is to provide an anti-cheating method based on the intelligent fitness set. The method defines that one movement is completed only when action standards are strictly complied with during the movement.

The objectives of the present disclosure can be achieved with technical solutions as follows.

An intelligent fitness set is provided, which includes a support, a base, a plurality of handheld fitness equipments and two handles. A processor, a movement posture sensor and a touch sensor are built in each of the two handles, and the movement posture sensor and the touch sensor are connected respectively to the processor. One end of each of the two handles is closed and a bayonet is provided at the other end of each of the two handles. The bayonet is switchable and hot-pluggable, configured to connect respectively to the plurality of handheld fitness equipments. A sensor and a pin connector matched with the bayonet are correspondingly provided in each of the plurality of handheld fitness equipments. A signal line is provided with the pin connector. The plurality of handheld fitness equipments are detachably fixed on the support, the two handles are placed on the base and the support is fixedly connected to the base. When the handles are connected to the plurality of handheld fitness equipments, the processor in each of the two handles receives an equipment identification number transmitted by each of the handheld fitness equipment via the pin connector, collects movement information of the corresponding handheld fitness equipment based on the equipment identification number, and uploads the movement information to a mobile terminal or a cloud server.

Preferably, the plurality of handheld fitness equipments comprise an abdominal wheel equipment, a push-up equipment, a jumping rope equipment and an elastic rope equipment. A pressure sensor and an infrared ranging device are built in the abdominal wheel equipment. And the pin connector matched with the bayonet of each of the two handles is provided at each of two ends of the abdominal wheel equipment. The pressure sensor, the infrared ranging device and an infrared line-crossing detection unit are built in the push-up equipment. The push-up equipment is divided into two portions. The pin connector matched with the bayonet of each of the handles is provided at a top of each of the portions. An infrared detector is built in the jumping rope equipment. The pin connector matched with the bayonet of each of the two handles is provided at each of two ends of the jumping rope equipment. A tension sensor is built in the elastic rope equipment. The pin connector matched with the bayonet of each of the two handles is provided respectively at an extension portion of the two ends of the elastic rope equipment. An opening is provided at another extension portion of the two ends of the elastic rope equipment for the handle to pass through.

Preferably, a first hole is provided at an upper portion of the support, and a second hole and a third hole are provided at a lower portion of the support. One portion of the push-up equipment is detachably fixed on the upper portion of the support after the pin connector of the push-up equipment is plugged into the first hole, and the other portion of the push-up equipment is detachably fixed on the lower portion of the support after the pin connector of the push-up equipment is plugged into the second hole. The abdominal wheel equipment is provided between the two portions of the push-up equipment. Two ends of the abdominal wheel equipment are plugged respectively into centers of the two portions of the push-up equipment via the pin connector. The jumping rope equipment is plugged into the third hole. A rope portion of the elastic rope equipment is hung on the support, such that the two ends of the elastic rope equipment are positioned respectively on a left and a right side of the support.

Preferably, an elastic button is provided on each of the two handles. An elastic clamping piece is provided on the pin connector of the abdominal wheel equipment, the push-up equipment and the jumping rope equipment or the elastic rope equipment corresponding to the elastic button. After each of the two handles is connected to the handheld fitness equipments, the handle will be locked by the elastic clamping piece on the pin connector. When the elastic button on the handle is pressed, the elastic clamping piece on the pin connector is pressed to move downward, enabling the handle to depart from each of the plurality of handheld fitness equipments.

Preferably, a power supply is built in each of the two handles, and the power supply is configured to power the processor, the movement posture sensor and the touch sensor.

Preferably, a photoelectric sensor is further built in each of the two handles, and the photoelectric sensor is connected to the processor.

Preferably, a heart rate sensor is further built in each of the two handles, and the heart rate sensor is connected to the processor.

Another object of the present invention can be achieved by adopting the following technical solution:

An anti-cheating method based on the intelligent fitness set, including: determining whether the user is cheating or not by the built-in processor in the handle based on data from the built-in sensor in the handle and data fed back from the sensor built in each of the plurality of handheld fitness equipments, when the two handles are connected to any one of the plurality of handheld fitness equipments.

Preferably, the method specifically includes the following steps:

1) detecting touch signals by the touch sensor when the user grasps the two handles with both hands, after the two handles are connected to any one of the plurality of handheld fitness equipments. If the handles are released from the hands, the touch induction is invalid and the action of the user is invalid, and the counts do not increase.

2) after the two handles are connected to an abdominal wheel device, the user is prevented from cheating through the following two detection methods:

2.1) detecting by the infrared ranging device built in the abdominal wheel equipment a number of rolling turns of the abdominal wheel equipment, converting the number of rolling turns into a rolling distance, and transmitting the rolling distance data to the processor built in the handle via signal lines of the pin connector. If the rolling distance fails to meet a standard requirement, it is determined that an action of the user is invalid.

2.2) placing a bodyweight on the abdominal wheel, transmitting a pressure data to the processor built in the handle the pressure sensor built in the abdominal wheel equipment via the signal lines of the pin connector when the user uses the abdominal wheel equipment. If the user grasps the handles with both hands and moves back and forth, rather than push the handles according to a standard movement, no pressure from the bodyweight can be detected by the handles, and the action of the user is invalid.

3) after the two handles are connected to a push-up device, the user is prevented from cheating through the following three detection methods:

3.1) detecting a distance between two portions of the push-up equipment, and transmitting the distance data to the processor built in the handle via signal lines of pin connector. If a distance fails to meet the standard requirement, the action of the user is invalid 3.2) transmitting detected data to the processor built in the handle by the infrared line-crossing detection unit built in the push-up equipment via the signal lines of the pin connector. If the user pushes down to reach or to exceed a standard line, the action of the user is correct; otherwise, the action of the user is invalid.

3.3) detecting a pressure applied to the push-up equipment by the pressure sensor built in the push-up equipment. If the user moves according to a standard action, a body pressure is applied through hands to the push-up equipment. The method further includes calculating the corresponding pressure data by the pressure sensor, and transmitting the pressure data to the processor built in the handle via the signal lines of the pin connector. If a posture of the user is incorrect, such that the pressure sensor fails to detect a pressure within a range, the action of the user is invalid.

4) after the two handles are connected to a jumping rope device, the user is prevented from cheating through the following two detection methods:

4.1) detecting the number of jumping turns of the user by the infrared detector built in the jumping rope equipment and transmitting an accumulated number of turns to the processor built in the handle by the infrared detector via signal lines of pin connector. If the user fails to complete one turn of jumping, the infrared detector detects that action of the user is substandard and the action of the user is invalid.

4.2) detecting a rotation direction of the user's jumping by the infrared detector built in the jumping rope equipment and transmitting the rotation direction data to the processor built in the handle via the signal lines of the pin connector. If a direction of the user's jumping is detected not consistent with the predefined direction, the action of the user is invalid.

5) after the two handles are connected to an elastic rope device, the user is prevented from cheating through the following two detection methods:

5.1) detecting a tension produced by the tension sensor when the elastic rope equipment is pulled and transmitting the tension data to the processor provided in the handle via signal lines of pin connector. If the elastic rope equipment is pulled by the user to a distance of the standard action, the tension sensor detects a tension data. If the elastic rope equipment is not pulled by the user to the distance of the standard action, the tension fails to meet a standard requirement, and the action of the user is invalid.

5.2) detecting a direction and an angle of the elastic rope equipment being pulled by the movement posture sensor provided in each handle, and determining by the handles whether the direction and the angle corresponding to an actual action meet a standard requirement based on action varieties set by the user. If the actual action fails to meet the standard requirement, the action of the user is invalid.

Preferably, in the step 4.2), the infrared detector built in the jumping rope equipment detects a rotation direction of jumping with a signal sequence transmitted by three infrared lamps.

As compared with the prior art, the present disclosure has the following beneficial effects.

1. Two handles are provided in the intelligent fitness set of the present invention. Each handle has a switchable and hot-pluggable bayonet which can be connected to a plurality of handheld fitness equipments. Moreover, a corresponding sensor and pin connector matched with the bayonets of the handles are provided on each of the plurality of handheld fitness equipment. When the handles are connected to the handheld fitness equipments, the processor provided in each handle receives an equipment identification number transmitted by the handheld fitness equipment via the pin connector, and collects movement information (e.g., movement count, whether movement action is correct, etc.) of the handheld fitness equipment based on the equipment identification number, and then uploads the movement information to a mobile terminal or a cloud server. Movement information of a plurality of handheld fitness equipments is collected through one same handle, simplifying the user's operation.

2. The intelligent fitness set of the present invention includes two intelligent fitness handles and a plurality of handheld fitness equipments. Preferably, the plurality of handheld fitness equipments are, respectively, the abdominal wheel equipment, the push-up equipment, the jumping rope equipment and the elastic rope equipment. The abdominal wheel equipment, the push-up equipment, the jumping rope equipment and the elastic rope equipment are provided with pin connector, such that the handles can be plugged respectively into the four handheld fitness equipments. Based on the equipment identification numbers transmitted by the pin connector, the handles can be switched to the movement modes of different handheld fitness equipments, and collect action feedback of different handheld fitness equipments, such that the handles can be reused by a plurality of handheld fitness equipments. One set of action training with a plurality of handheld fitness equipments can be performed with one same set of handles. The structure is simple and the cost is low.

3. The intelligent fitness set of the present disclosure provides a support and a base. The four handheld fitness equipments are detachably fixed on the support. The two handles are placed on the base, and the support is fixedly connected to the base. As such, the entire set has an attractive overall appearance and is compact, suitable for use in various places.

4. Each of the handheld fitness equipments in the intelligent fitness set of the present disclosure is provided with more than one electronic movement detection techniques, normalizing the completion standard of each action. As such, action is normalized, and a movement is completed only when standards are strictly complied with, so to achieve anti-cheating.

Figure 1:
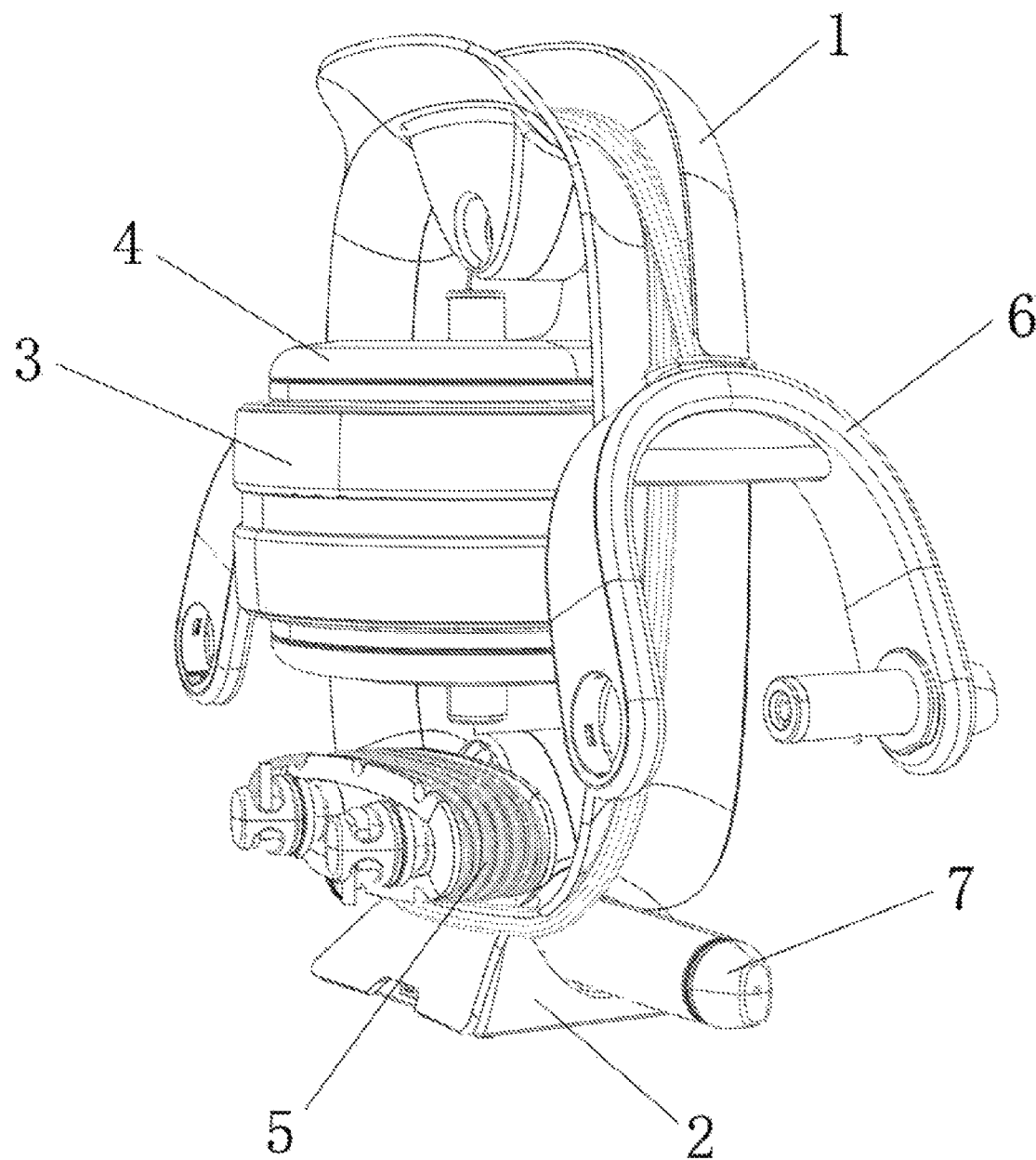
FIG. 1 is a structural diagram of an intelligent fitness set according to an embodiment of the present disclosure.

In the drawings, reference numerals and components denoted thereby are as follows:

1. support; 2. base; 3. abdominal wheel equipment; 4. push-up equipment; 5. jumping rope equipment; 6. elastic rope equipment; 7. handle; 8. first hole; 9. second hole; 10. third hole; 11. bayonet; 12. first pin connector; 13. second pin connector; 14. third pin connector; 15. fourth pin connector; 16. opening; 17. elastic button; 18. elastic clamping piece.

DETAILED DESCRIPTION OF THE PRESENT INVENTION

The present disclosure will be described below in further detail in conjunction with embodiments and the accompanying drawings, but the implementations of the present disclosure are not limited thereto.

Embodiment 1

Figure 2:
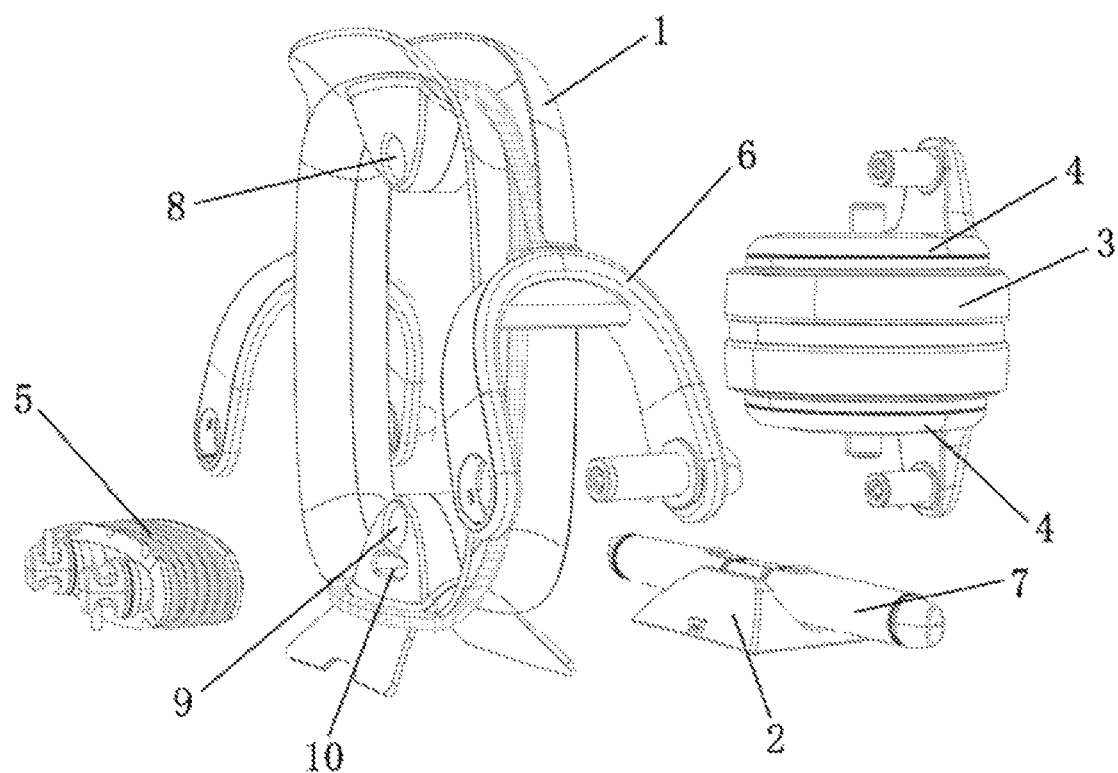
FIG. 2 is an exploded structural diagram of the intelligent fitness set according to an embodiment of the present disclosure.

As shown in FIGS. 1 and 2, the intelligent fitness set of this embodiment includes the support 1, the base 2, the abdominal wheel equipment 3, the push-up equipment 4, the jumping rope equipment 5, the elastic rope equipment 6 and two handles 7. The upper portion of the support 1 is provided with the first hole 8, and the lower portion of the same is provided with the second hole 9 and the third hole 10.

Figure 3:
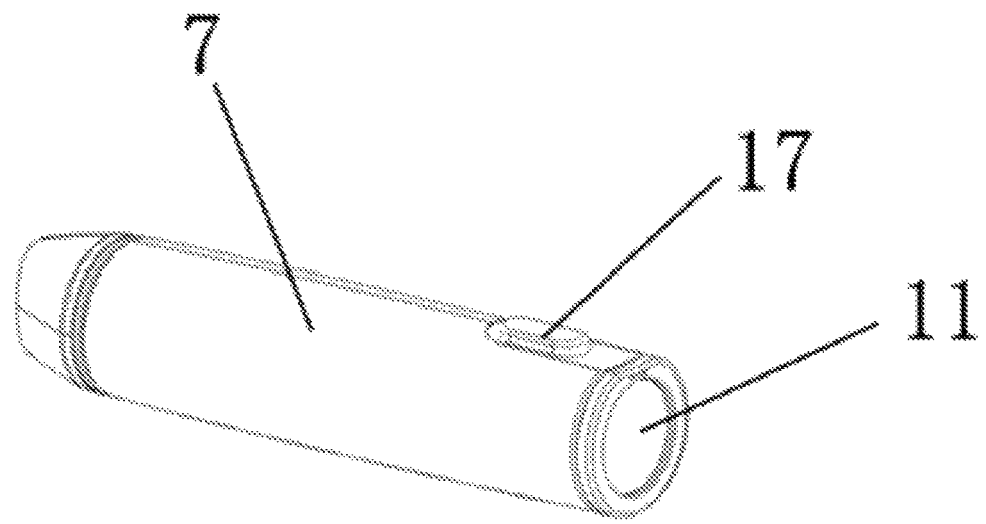
FIG. 3 is a structural diagram of a handle according to an embodiment of the present disclosure.

As shown in FIG. 3, one end of each handle 7 is closed, while the other end of the handle is provided with a bayonet 11. The bayonet 11 is a switchable hot-pluggable bayonet, configured to connect respectively to the abdominal wheel equipment 3, the push-up equipment 4, the jumping rope equipment 5 and the elastic rope equipment 6.

Figure 4:
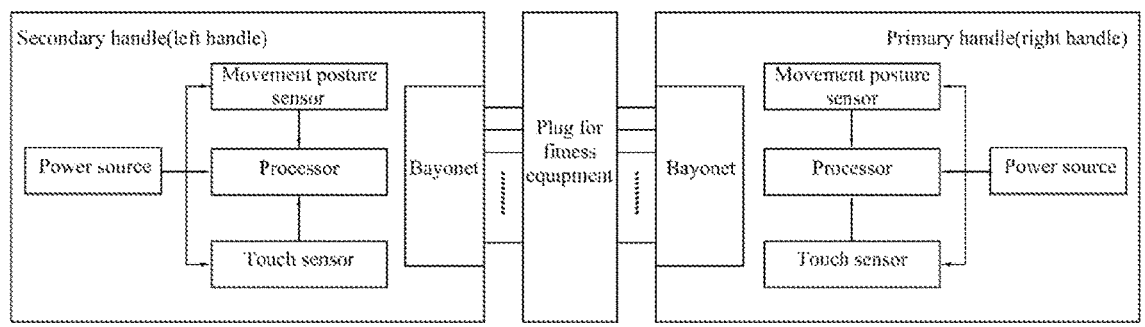
FIG. 4 is a functional block diagram illustrating the connection of two handles with handheld fitness equipment according to an embodiment of the present disclosure.

As shown in FIG. 4, each of the two handles 7 is provided therein with the processor, the movement posture sensor, the touch sensor and the power supply. The movement posture sensor and the touch sensor are connected respectively with the processor. The processor is an ARM processor that can be provided on a circuit board. The movement posture sensor is a six-axis movement posture sensor that can detect the direction, angle and other postures of the elastic rope equipment 6 when it is pulled. The touch sensor is used to detect a touch signal when the handles 7 are grasped by a user. The power supply is a lithium ion battery configured to power the processor, the movement posture sensor and the touch sensor.

After the two handles 7 are connected to any one of the handheld fitness equipments, two touch sensors detect touch signals when a user grasps the two handles with both hands. When the handles are released from the hands (including the situation in which the hands fail to grasp the handles tightly), touch induction is invalid. As such, it is determined that action of the user is invalid, and there is no increase in counts.

One of the two handles 7 may be taken as the primary handle (right handle), and the other one may be taken as the secondary handle (left handle). The primary handle may be provided therein with an RF (Radio Frequency) antenna and a BLE (Bluetooth Low Energy) antenna through which communicates with the mobile terminal. The secondary handle may be provided therein with an RF antenna through which communicates with the mobile terminal.

Figure 5:
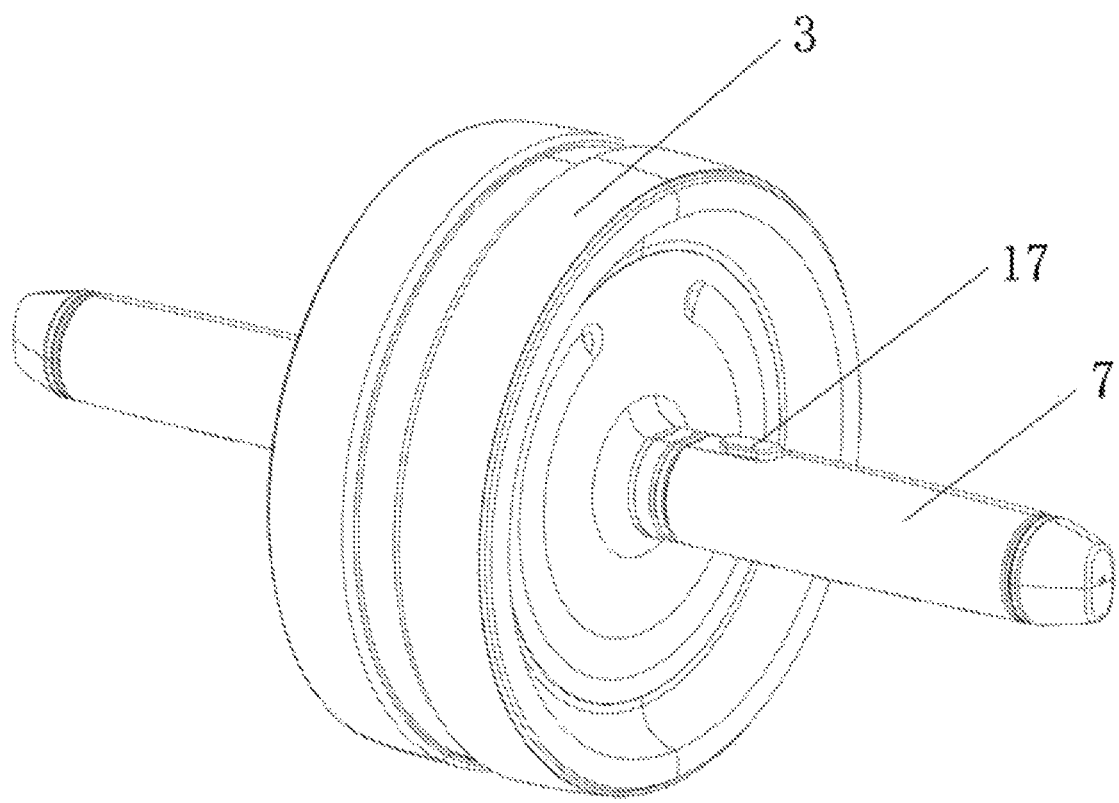
FIG. 5 is a schematic diagram of the handles after being connected to an abdominal wheel equipment according to an embodiment of the present disclosure.
Figure 6:
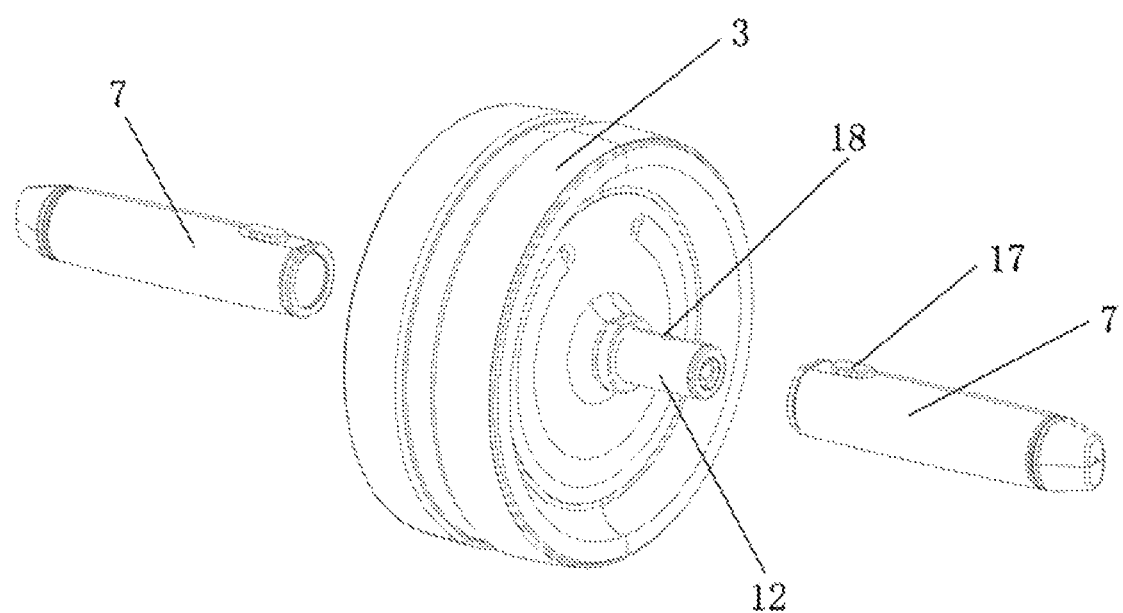
FIG. 6 is a schematic diagram of the handles after being withdrawn from the abdominal wheel equipment according to an embodiment of the present disclosure.

As shown in FIGS. 5 and 6, two ends of the abdominal wheel equipment 3 are provided respectively with a first pin connector 12 matched with the bayonet 11 of a corresponding handle 7. Each of the first pin connector 12 is provided with a signal line.

Figure 7:
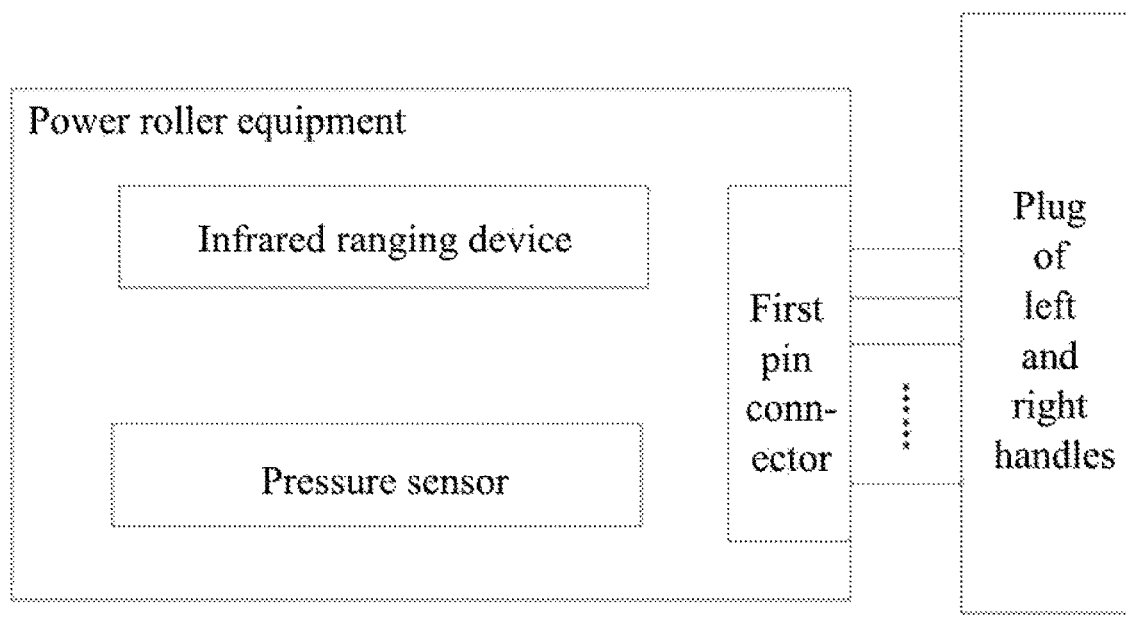
FIG. 7 is a functional block diagram illustrating the connection of the handles with the abdominal wheel equipment according to an embodiment of the present disclosure.

As shown in FIG. 7, the abdominal wheel equipment 3 is provided therein with a pressure sensor and an infrared ranging device. The pressure sensor is configured to detect a weight applied to the abdominal wheel equipment 3 by the human body when a user uses the abdominal wheel equipment 3. The infrared ranging device is configured to detect the number of rolling turns of the abdominal wheel equipment 3 and to convert it into a specific distance. When the first pin connector 12 are plugged into the bayonets 11 of the handles 7, the pressure sensor and the infrared ranging device may transmit the detected data to the processors via the signal lines of the first pin connector 12. After the two handles 7 are connected to the abdominal wheel equipment 3, the user is prevented from cheating through the following two detection methods:

1) avoiding insufficiency of the rolling distance of the abdominal wheel. When the user is using the abdominal wheel equipment, the infrared ranging device provided in the abdominal wheel equipment detects the number of rolling turns of the abdominal wheel equipment, converts the number of rolling turns into a specific rolling distance, and transmits this rolling distance data to the processor provided in each handle via the signal lines of the first pin connector 12. If the rolling distance fails to meet a standard requirement (i.e. that the rolling distance reaches a set threshold), the action of the user is invalid.

2) avoiding the situation in which the user assumes improper postures or cheats by pushing fraudulently: when the user is using the abdominal wheel equipment, a body weight is placed on the abdominal wheel. The pressure sensor provided in the abdominal wheel equipment transmits this pressure data to the processor provided in each handle via the signal lines of the first pin connector 12. If the user grasps the handles with both hands and moves back and forth, rather than push the handles according to a standard action, no pressure from the human body can be detected by the handles, such that the action of the user is determined invalid.

Figure 8:
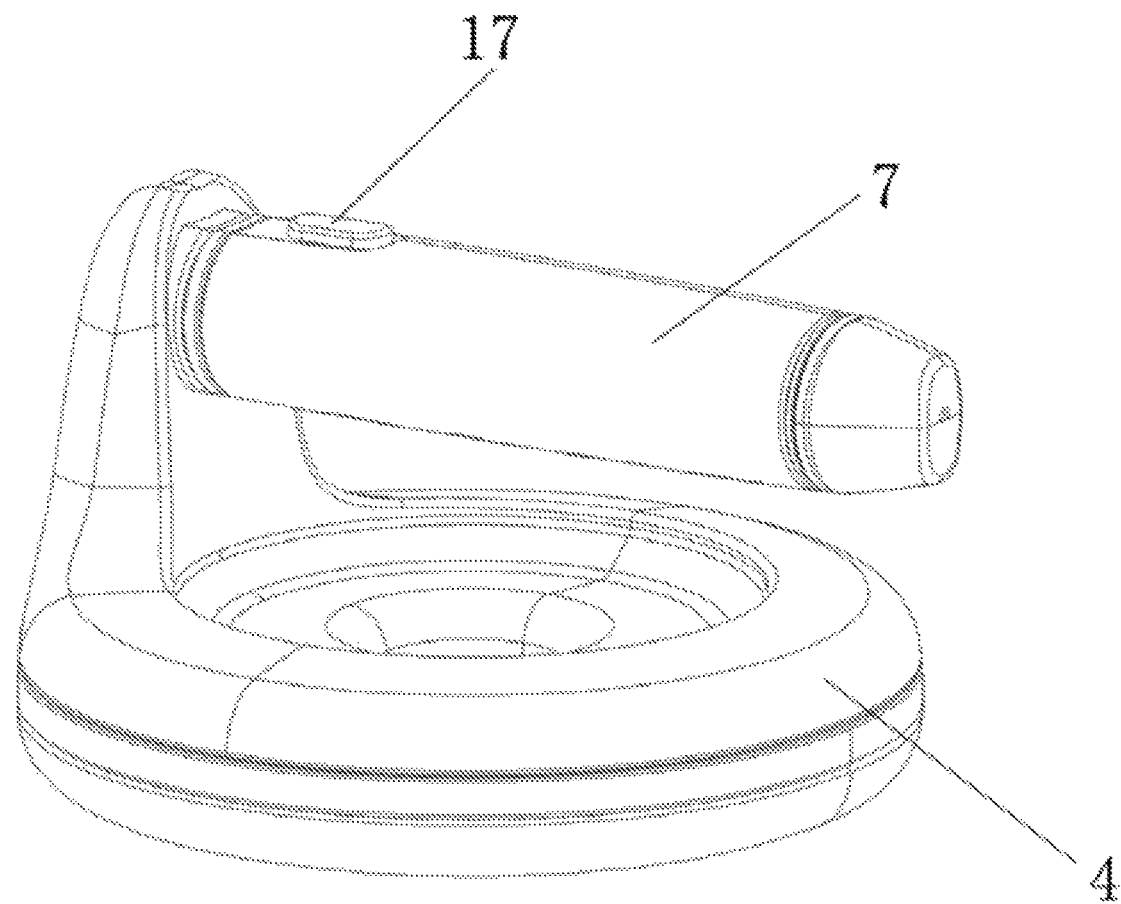
FIG. 8 is a schematic diagram of a handle after being connected to a portion of a push-up equipment according to an embodiment of the present disclosure.
Figure 9:
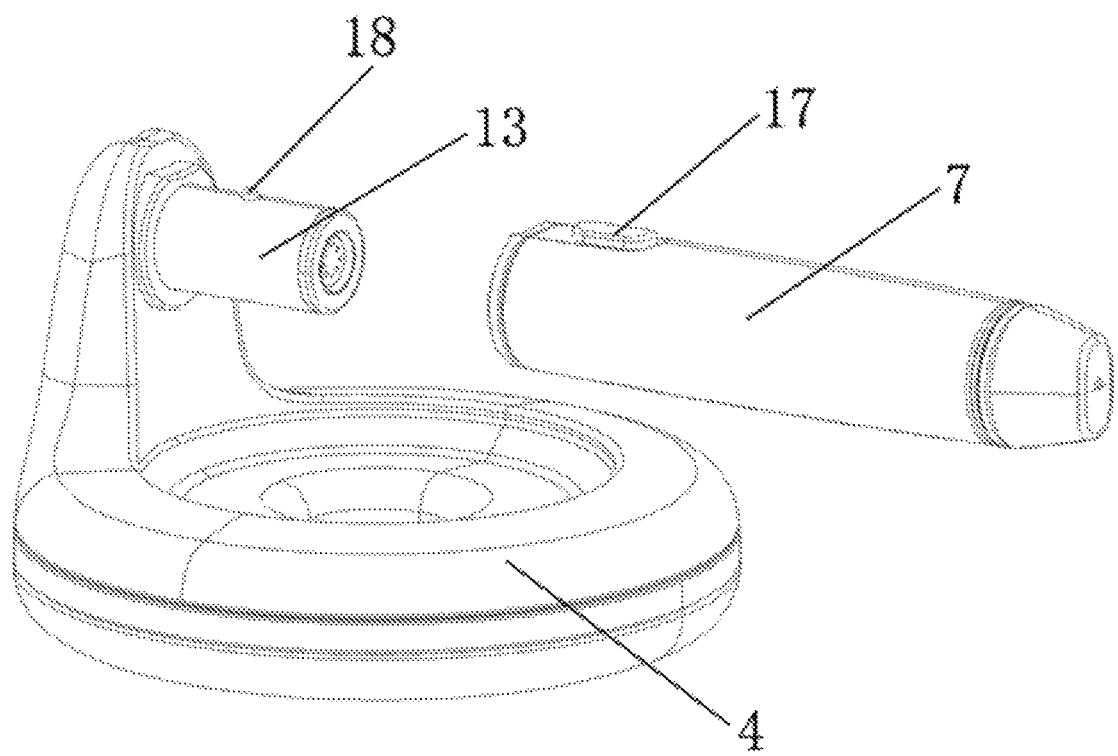
FIG. 9 is a schematic diagram of the handle after being withdrawn from the portion of the push-up equipment according to an embodiment of the present disclosure.

As shown in FIGS. 8 and 9, the push-up equipment 4 is composed of two portions (only one of the two portions is shown). The top of each portion is provided with a second pin connector 13 matched with the bayonet 11 of a corresponding handle 7, and each of the second pin connector 13 is provided with a signal line.

Figure 10:
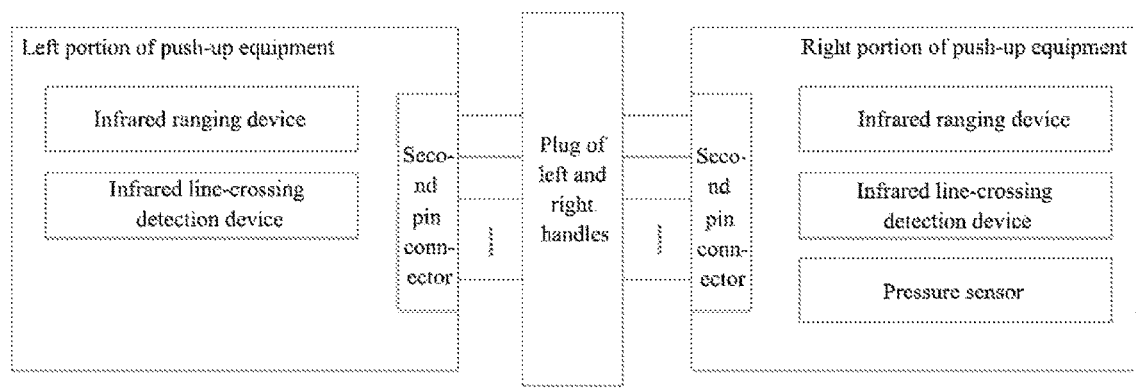
FIG. 10 is a functional block diagram illustrating the connection of the handle with the push-up equipment according to an embodiment of the present disclosure.

As shown in FIG. 10, the push-up equipment 4 is provided with a pressure sensor, an infrared ranging device (an infrared transmitter is provided in the left portion of the push-up equipment 4, and an infrared receiver is provided in the right portion of the push-up equipment 4. Both the infrared emitter and the infrared receiver are provided with two infrared lamps) and an infrared line-crossing detection unit (an infrared emitter is provided in the left portion of the push-up equipment 4. The infrared receiver is provided in the right portion of the push-up equipment 4). The pressure sensor is used for detecting pressure applied to the push-up equipment 4 by the user with hands. When the second pin connector 13 are plugged into the bayonets 11 of the handles 7, the pressure sensor, the infrared ranging equipment and the infrared line-crossing detection unit may transmit the detected data to the processors via the signal lines of the second pin connector 13. After the two handles 7 are connected to the push-up equipment 4, the user is prevented from cheating through the following three detection methods:

1) avoiding a deficient distance between the two portions of the push-up equipment: when the user is using the push-up equipment, the infrared ranging device provided in the push-up equipment detects a distance between the two portions of the push-up equipment, and transmits this distance data to the processor provided in each handle via the signal lines of the second pin connector 13. If this distance fails to meet a standard requirement, the action of the user is invalid.

2) avoiding the user's failure to push down his body to be below the line: when the user is using the push-up equipment, the infrared line-crossing detection unit provided in the push-up equipment transmits the detected data to the processor provided in each handle via the signal lines of the second pin connector 13. If the user pushes down to reach a standard line, the action of the user is correct; otherwise, the action of the user is invalid.

3) avoiding a deceptive action: when the user is using the push-up equipment, the pressure sensor provided in the push-up equipment detects pressure applied to the push-up equipment. If the user moves according to a standard action, a body pressure will be applied through hands to the push-up equipment. The pressure sensor calculates the pressure data correspondingly, and transmits this pressure data to the processor provided in each handle via the signal lines of the second pin connector 13. If postures of the user are incorrect, such that the pressure sensor fails to detect a pressure within a corresponding range, the action of the user is invalid.

Figure 11:
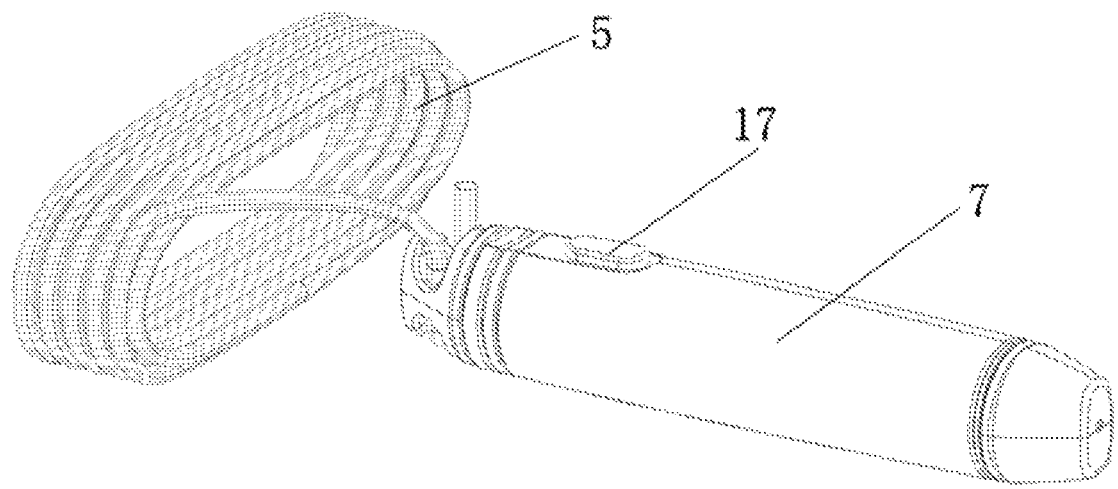
FIG. 11 is a schematic diagram of a handle after being connected to an end of a jumping rope equipment according to an embodiment of the present disclosure.
Figure 12:
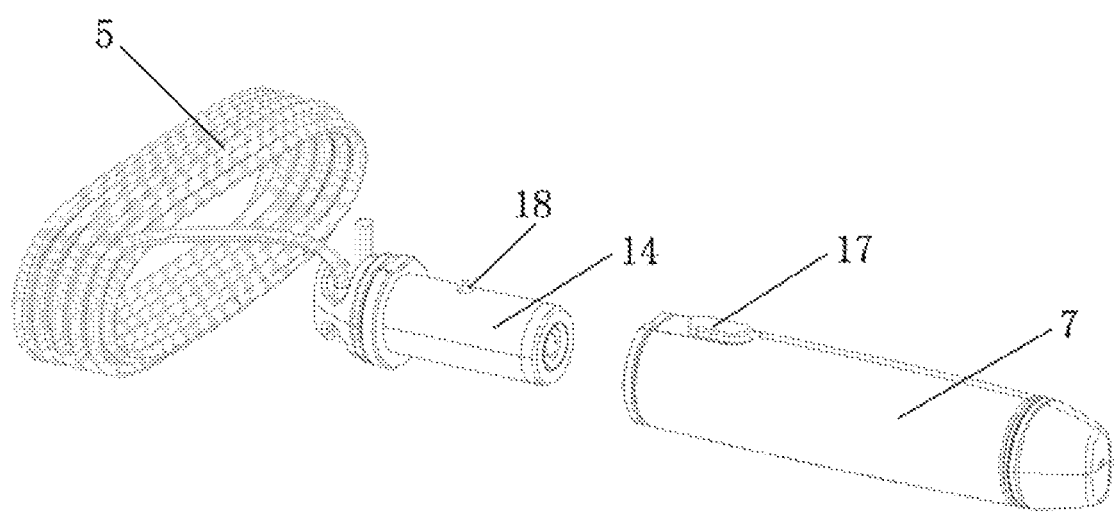
FIG. 12 is a schematic diagram of the handle after being withdrawn from the end of the jumping rope equipment according to an embodiment of the present disclosure.

As shown in FIGS. 11 and 12, two ends (only one of the two ends is shown) of the jumping rope equipment 5 are provided respectively with a third pin connector 14 matched with the bayonet 11 of a corresponding handle 7. Each of the third pin connector 14 is provided with a signal line.

Figure 13:
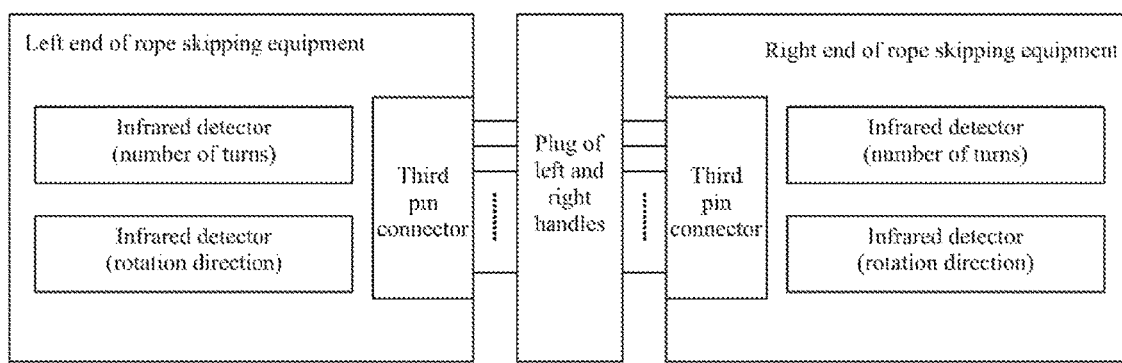
FIG. 13 is a functional block diagram illustrating the connection of the handle with the jumping rope equipment according to an embodiment of the present disclosure.

As shown in FIG. 13, the jumping rope equipment 5 is provided therein with an infrared detector for detecting the number of jumping turns and the jumping direction of the user. When the third pin connector 14 are plugged into the bayonets 11 of the handles 7, the infrared detector may transmit the detected data to the processors via the signal lines of the third pin connector 14. After the two handles are connected to the jumping rope equipment, the user is prevented from cheating through the following two detection methods:

1) avoiding the cheating behavior of artificially increasing the number of jumping counts: when the user is using the jumping rope equipment, the infrared detector provided in the jumping rope equipment detects the number of jumping turns of the user. When the user completes one turn of jumping, a corresponding infrared detector will revolve for one time, and if the user fails to complete one turn of jumping, the infrared detector will detect that action of the user is substandard and thus determine that this action of the user is invalid. Finally, the infrared detector transmits the accumulated number of turns to the processor provided in each handle via the signal lines of the third pin connector 14.

2) avoiding confusion of actions: when the user is using the jumping rope equipment, the infrared detector provided in the jumping rope equipment detects the rotation direction along which the user skips, such as forward-jumping direction, backward-jumping direction, cross-jumping direction, etc., using a signal sequence transmitted by three infrared lamps. This rotation direction data may be transmitted to the processor provided in each handle via the signal lines of the third pin connector 14. If it is detected that the direction along which the user skips is not consistent with the predefined direction (for example, the predefined direction is a forward-jumping direction, while the user skips in a backward-jumping direction), it is determined that action of the user is invalid.

Figure 14:
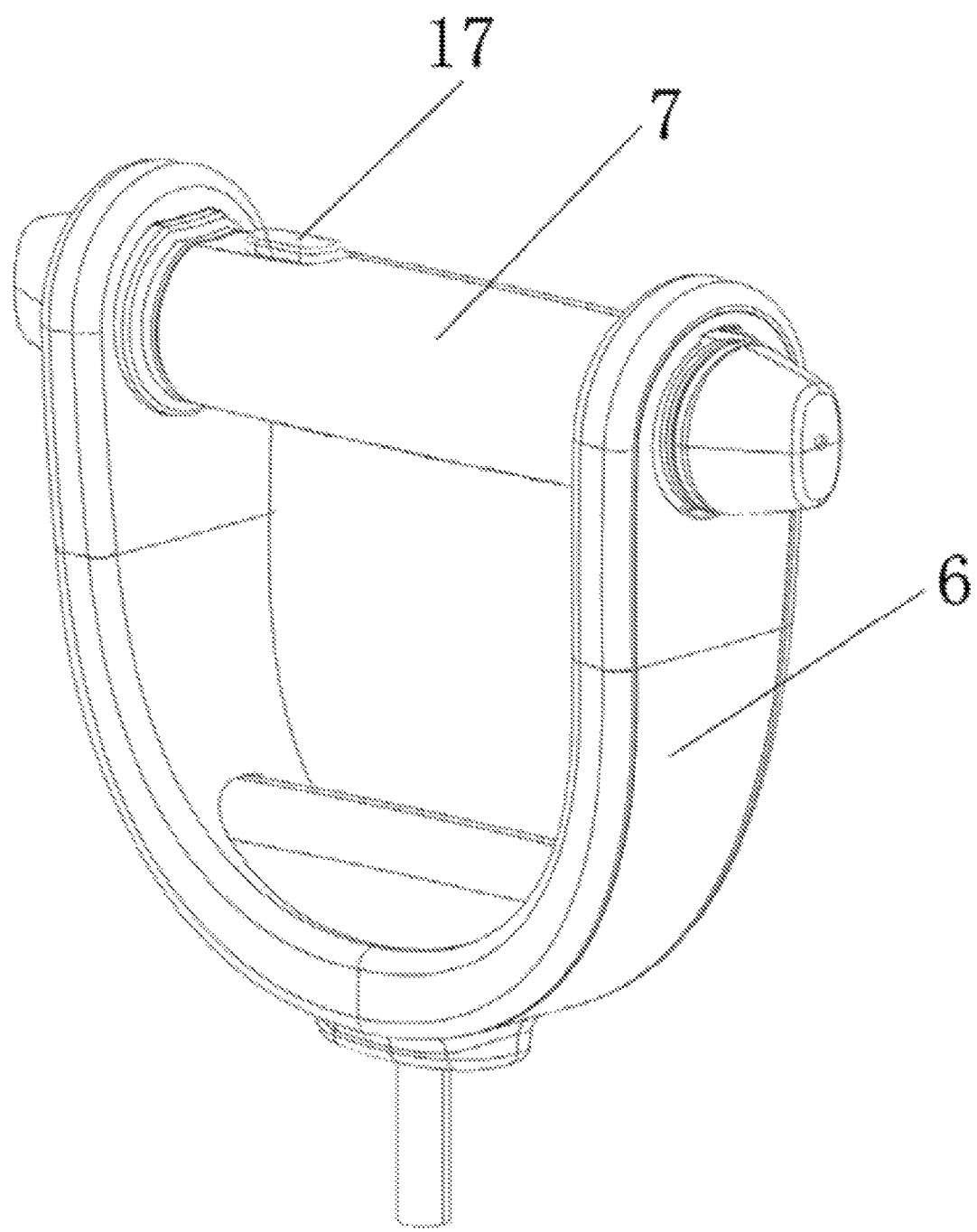
FIG. 14 is a schematic diagram of a handle after being connected to an end of an elastic rope equipment according to an embodiment of the present disclosure.
Figure 15:
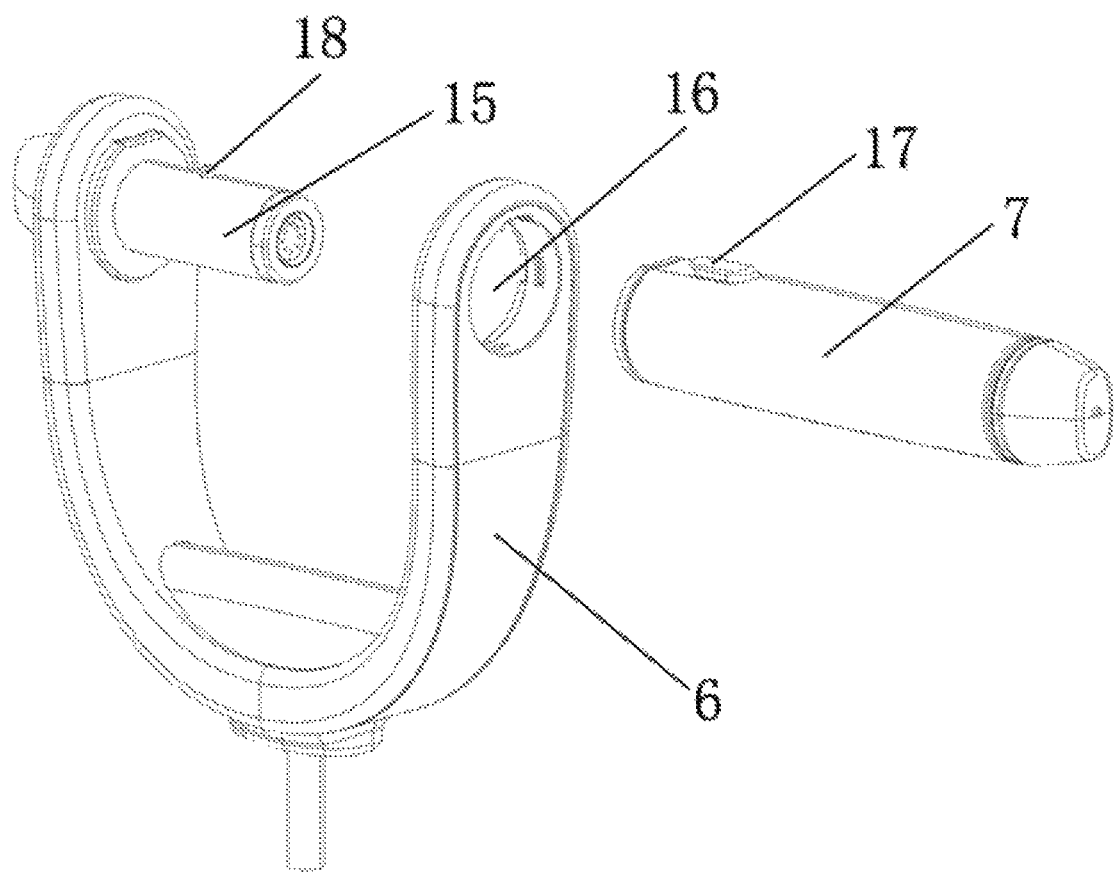
FIG. 15 is a schematic diagram of the handle after being withdrawn from the end of the elastic rope equipment according to an embodiment of the present disclosure.

As shown in FIGS. 14 and 15, an extension portion at each of the two ends (only one of the two ends is shown) of the elastic rope equipment 6 is provided with a fourth pin connector 15 matched with the bayonet 11 of a corresponding handle 7, while the other extension portion at each of the two ends of the elastic rope equipment is provided with an opening 16 for the corresponding handle 7 to pass through, wherein each of the fourth pin connector 15 is provided with a signal line.

Figure 16:
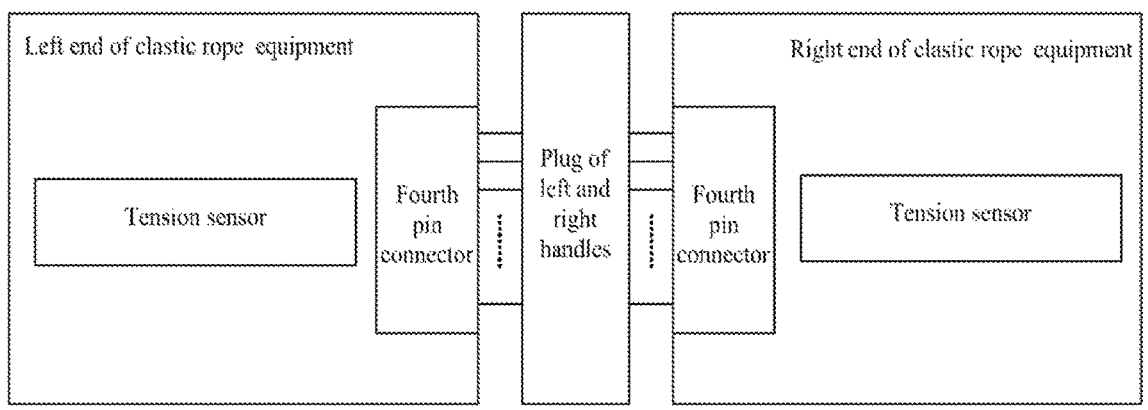
FIG. 16 is a functional block diagram illustrating the connection of the handle with the elastic rope equipment according to an embodiment of the present disclosure.

As shown in FIG. 16, the elastic rope equipment 6 is provided therein with a tension sensor for detecting the tension data of the user; when the fourth pin connector 15 are plugged into the bayonets 11 of the handles 7, the tension sensor may transmit the detected data to the processors via the signal lines of the fourth pin connector 15. After the two handles are connected to the elastic rope equipment, the user is prevented from cheating through the following two detection methods:

1) when the user uses the elastic rope equipment, the tension sensor provided in the elastic rope equipment detects the tension produced when the elastic rope equipment is pulled. A rope portion of the elastic rope equipment is an elastic material. As such, when the rope portion is tensioned and deformed within the elastic range, the length of deformation is in direct proportion to the tension. Therefore, if the elastic rope equipment is pulled by the user to the distance of a standard action, the tension sensor will detect a corresponding tension data, and transmit this tension data to the processor provided in each handle via the signal lines of the fourth pin connector 15. If the elastic rope equipment is not pulled by the user to the distance of the standard action, tension fails to meet a standard requirement, and it is determined that the action of the user is invalid.

2) when the user is using the elastic rope equipment, the movement posture sensor provided in each handle detects the direction, angle and other postures of the elastic rope equipment when it is pulled. When the elastic rope is pulled in various manners, the handles will move at different angles along forward, backward, leftward, rightward, upward, downward and slanting directions. The handles determine whether the direction and angle corresponding to an actual action meet the standard requirement based on action varieties set by the user. If the actual action fails to meet the standard requirement, the action of the user is invalid.

As shown in FIGS. 3-16, each of the handles 7 is provided thereon with an elastic button 17. elastic clamping pieces 18 are provided respectively at positions on the first pin connector 12, the second pin connector 13, the third pin connector 14 and the fourth pin connector 15 that correspond to the elastic buttons 17. After the handles 7 are connected to any one of the handheld fitness equipments, they will be locked by the elastic clamping pieces 18 on the pin connector of the handheld fitness equipment, and when the elastic buttons 17 on the handles 7 are pressed, the elastic clamping pieces 18 on the pin connector of this handheld fitness equipment are pressed to move downward, such that the handles 7 can be released from this handheld fitness equipment.

The working principle of this embodiment is as follows. When the two handles 7 are connected to any one of the handheld fitness equipments, the processor provided in each handle 7 receives the equipment identification number transmitted by this handheld fitness equipment via the pin connector. Then, it may start to conduct counting for this handheld fitness equipment, collect movement information (e.g., movement count, whether movement action is correct, etc.) of this handheld fitness equipment based on the equipment identification number, and then upload this movement information to an APP (application) of the mobile terminal, such that the mobile terminal can collect the movement information of this handheld fitness equipment in a real-time manner. When the handles are switched to the next handheld fitness equipment, they will automatically identify the identification number thereof, and in the meantime, upload it to the APP of the mobile terminal so as to count up different movement information.

As shown in FIGS. 1-16, one of the two portions of the push-up equipment 4 is detachably fixed on the upper portion of the support 1 after the second pin connector 13 thereof is plugged into the first hole 8. The other one of the two portions of the push-up equipment is detachably fixed on the lower portion of the support 1 after the second pin connector 13 thereof is plugged into the second hole 9. The abdominal wheel equipment 3 is provided between the two portions of the push-up equipment 4. Two ends of the abdominal wheel equipment are plugged respectively into the centers of the two portions of the push-up equipment 4 through the first pin connector 12. The jumping rope equipment 5 is plugged into the third hole 10. A rope portion of the elastic rope equipment 6 is hung on the support 1, such that the two ends of the elastic rope equipment 6 are positioned respectively on the left and right sides of the support 1. The two handles 7 are placed on the base 2, and the support 1 is fixedly connected to the base 2.

Embodiment 2

The main features of this embodiment are as follows: when the handles 7 are connected to any one of the handheld fitness equipments, the processor provided in each handle 7 receives the equipment identification number transmitted by this handheld fitness equipment via pin connector. Then, it may start counting for this handheld fitness equipment, collect movement information (e.g., movement count, whether movement action is correct, etc.) of this handheld fitness equipment based on the equipment identification number, and then upload this movement information to the cloud server. Other contents are the same as those of embodiment 1.

Embodiment 3

The main features of this embodiment are as follows: each of the two handles 7 is further provided therein with a photoelectric sensor (for counting), a heart rate sensor, a distance measuring sensor, a pressure sensor, etc. These sensors are connected respectively with the processors. Other contents are the same as those of Embodiment 1.

Embodiment 4

The main features of this embodiment are as follows. The intelligent fitness set may further comprise such handheld fitness equipments as kettlebells, dumbbells, power twisters, wrist exercising equipment and sit-up equipment. Other contents are the same as those of embodiment 1.

The mobile terminal in the above embodiment may be a smart phone, a PDA handheld terminal, a tablet computer, an electronic book, a man-machine interaction terminal or other handheld terminal equipment with displaying functions.

In conclusion, the intelligent fitness set of the present disclosure is provided with two handles, each of which has a switchable and hot-pluggable bayonet that can be connected to a plurality of handheld fitness equipments. Moreover, a corresponding sensor and pin connector matched with the bayonets of the handles are provided on each handheld fitness equipment. When the handles are connected to a corresponding one of the fitness equipments, the processor provided in each handle receives an equipment identification number transmitted by the corresponding fitness equipment via the pin connector, collects movement information (e.g., movement count, whether movement action is correct, etc.) of the corresponding fitness equipment based on the equipment identification number, and then uploads the movement information to a mobile terminal or a cloud server. Movement information of a plurality of handheld fitness equipments is collected through one same handle, simplifying the user's operation. Meanwhile, each of the handheld fitness equipments in the intelligent fitness set of the present disclosure is provided with more than one electronic movement detection techniques, normalizing the completion standard of each action. As such, action is normalized, and a movement is completed only when standards are strictly complied with, so to achieve anti-cheating.

What have been described above are merely preferred embodiments of the present disclosure patent, and the scope of protection of the present disclosure patent is not limited thereto. Without departing from the scope disclosed by the present patent disclosure, the equivalents or changes that are made to the technical solution and inventive concept of the present disclosure patent by those technicians familiar with the technical field shall be covered by the scope of protection of the present patent application.

What is claimed is:

1. An intelligent fitness set, comprising: a support, a base, a plurality of handheld fitness equipments and two handles;
   wherein a processor, a movement posture sensor and a touch sensor are built in each of the two handles;
   the movement posture sensor and the touch sensor are connected respectively to the processor;
   one end of each of the two handles is closed; a bayonet is provided at the other end of each of the two handles;
   the bayonet is switchable and hot-pluggable, and configured to connect respectively to any one of the plurality of handheld fitness equipments when the two handles and the plurality of handheld fitness equipments are disassembled from the fitness set;
   a sensor and a pin connector matched with the bayonet of each of the two handles are correspondingly provided on each of the plurality of handheld fitness equipments;
   a signal line is provided with the pin connector;
   the plurality of handheld fitness equipments are detachably fixed on the support;
   the two handles are placed on the base when in an assembled form;
   the support is fixedly connected to the base;
   when the handles are disassembled from the fitness set and are connected to any one of the plurality of handheld fitness equipments, the processor in each of the two handles is configured to:
   receive an equipment identification number transmitted by the corresponding handheld fitness equipment via the pin connector, collect movement information of the corresponding handheld fitness equipment based on the equipment identification number, and upload the movement information to a mobile terminal or a cloud server;
   when a user grasps the two handles with both hands, the touch sensor detects touch signals, and when the two handles are released from both hands of the user, touch induction is invalid and an action of the user is invalid, and a count of the action will not increase; wherein the two handles detaching from both hands comprises both hands failing to grasp tight;
   the plurality of handheld fitness equipments comprise an abdominal wheel equipment, a push-up equipment, a jumping rope equipment and an elastic rope equipment;
   wherein the abdominal wheel equipment comprises a first pressure sensor and a first infrared ranging device built in the abdominal wheel equipment; the pin connector of the abdominal wheel matched with the bayonet of each of the two handles is provided at each of two ends of the abdominal wheel equipment;
   the push-up equipment comprises a second pressure sensor, a second infrared ranging device and a first infrared line-crossing detection unit built in the push-up equipment; the push-up equipment is divided into two portions; wherein the pin connector of the push-up equipment matched with the bayonet of each of the two handles is provided at a top of each of the two portions;
   the jumping rope equipment comprises an infrared detector built in the jumping rope equipment; the pin connector of the jumping rope equipment matched with the bayonet of each of the two handles is provided at each of two ends of the jumping rope equipment;
   the elastic rope equipment comprises two ends and a tension sensor built in the elastic rope equipment;
   the pin connector of the elastic rope equipment matched with the bayonet of each of the two handles is provided respectively at an extension portion of the two ends of the elastic rope equipment; an opening is provided at another extension portion of the two ends of the elastic rope equipment for receiving one of the two handles;
   a first hole is provided at an upper portion of the support, and a second hole and a third hole are provided at a lower portion of the support;
   one portion of the push-up equipment is detachably fixed on the upper portion of the support after the pin connector of the push-up equipment is plugged into the first hole; the other portion of the push-up equipment is detachably fixed on the lower portion of the support after the pin connector of the push-up equipment is plugged into the second hole;
   the abdominal wheel equipment is provided between the two portions of the push-up equipment when being assembled in the fitness set; the pin connector at each of the two ends of the abdominal wheel equipment are plugged respectively into centers of the two portions of the push-up equipment;
   the jumping rope equipment is plugged into the third hole;
   a rope portion of the elastic rope equipment is hung on the support, such that the two ends of the elastic rope equipment are positioned respectively on a left and a right side of the support.

2. The intelligent fitness set of claim 1, wherein an elastic button is provided on each of the two handles;
   an elastic clamping piece is provided on the pin connector of the abdominal wheel equipment, the push-up equipment, the jumping rope equipment and the elastic rope equipment corresponding to the elastic button on each of the two handles;

the two handles are locked by the elastic clamping piece on the pin connector after each of the two handles is connected to the corresponding handheld fitness equipment; and when the elastic button on each of the two handles is pressed, the elastic clamping piece on the pin connector is pressed to move downward, enabling each of the two handles to depart from the corresponding handheld fitness equipment.

3. The intelligent fitness set of claim 1, wherein a power supply is built in each of the two handles, and the power supply is configured to power the processor, the movement posture sensor and the touch sensor.

4. The intelligent fitness set according to claim 1, wherein a photoelectric sensor is further built in each of the two handles, and the photoelectric sensor is connected to the processor.

5. The intelligent fitness set according to claim 1, wherein a heart rate sensor is further built in each of the two handles, and the heart rate sensor is connected to the processor.

6. An anti-cheating method based on the intelligent fitness set of claim 1, comprising:

determining whether the user is cheating or not by the built-in processor in each of the two handles based on data from the movement posture sensor and the touch sensor built in each of the two handles and data fed back from the sensor built in each of the plurality of handheld fitness equipments, when the two handles are connected to any one of the plurality of handheld fitness equipments.

7. The anti-cheating method of claim 6, wherein the method further comprises:

detecting touch signals by the touch sensor when the user grasps the two handles with both hands, after the two handles are connected to any one of the plurality of handheld fitness equipments; wherein if the two handles are released from both hands, the touch induction is invalid and the action of the user is invalid, and the counts of the action does not increase; wherein when the two handles are connected to the abdominal wheel equipment, the method comprises:

detecting by the infrared ranging device built in the abdominal wheel equipment a number of rolling turns of the abdominal wheel equipment, converting the number of rolling turns into a rolling distance, and transmitting the rolling distance data to the processor built in each of the two handles via signal lines of the pin connector; wherein if the rolling distance fails to meet a standard requirement, it is determined that an action of the user is invalid; or placing a bodyweight on the abdominal wheel, transmitting a pressure data from the first pressure sensor built in the abdominal wheel equipment to the processor built in each of the two handles via the signal lines of the pin connector when the user uses the abdominal wheel equipment; wherein if the user grasps the two handles with both hands and moves back and forth, rather than push the two handles according to a standard movement, no pressure from the bodyweight can be detected by the two handles, and the action of the user is invalid;

when the two handles are connected to the push-up equipment, the method comprises:

detecting a distance between two portions of the push-up equipment, and transmitting the distance data to the processor built in each of the two handles via signal lines of pin connector; wherein if the distance fails to meet a set threshold, the action of the user is invalid; or transmitting detected data to the processor built in each of the two handles by the infrared line-crossing detection unit built in the push-up equipment via the signal lines of the pin connector; wherein if the user pushes down to reach or to exceed a standard line, the action of the user is correct; otherwise, the action of the user is invalid; or detecting a pressure applied to the push-up equipment by the second pressure sensor built in the push-up equipment; wherein if the user moves according to a standard action, a body pressure is applied through hands to the push-up equipment; calculating the corresponding pressure data by the second pressure sensor, and transmitting the pressure data to the processor built in each of the two handles via the signal lines of the pin connector; wherein if a posture of the user is incorrect, such that the second pressure sensor fails to detect a pressure within a range, the action of the user is invalid;

when the two handles are connected to the jumping rope equipment, the method comprises:

detecting the number of jumping turns of the user by the infrared detector built in the jumping rope equipment; and transmitting an accumulated number of turns to the processor built in each of the two handles by the infrared detector via signal lines of pin connector; wherein if the user fails to complete one turn of jumping, the infrared detector detects that action of the user is substandard and the action of the user is invalid; or detecting a rotation direction of the user's jumping by the infrared detector built in the jumping rope equipment; transmitting the rotation direction data to the processor built in each of the two handles the signal lines of the pin connector; wherein if the rotation direction of the user's jumping detected is not consistent with a predefined direction, the action of the user is invalid; and when the two handles are connected to the elastic rope equipment, the method comprises:

detecting a tension produced by the tension sensor when the elastic rope equipment is pulled; transmitting a tension data to the processor provided in each of the two handles via signal lines of pin connector; wherein if the elastic rope equipment is pulled by the user to a distance of the standard action, the tension sensor detects the tension data; if the elastic rope equipment is not pulled by the user to the distance of the standard action, the tension fails to meet a standard requirement, and the action of the user is invalid; or detecting a direction and an angle of the elastic rope equipment being pulled by the movement posture sensor provided in each of the two handles, and determining by the two handles whether the direction and the angle detected corresponding to an actual action meet a standard requirement based on action varieties set by the user; wherein if the actual action fails to meet the standard requirement, the action of the user is invalid.

8. The anti-cheating method of claim 7, wherein the infrared detector built in the jumping rope equipment detects the rotation direction of jumping with a signal sequence transmitted by three infrared lamps.

* * * * *